(12) United States Patent
Kitada et al.

(10) Patent No.: US 10,249,034 B2
(45) Date of Patent: Apr. 2, 2019

(54) SUBSTRATE DEFECT INSPECTION APPARATUS, METHOD OF ADJUSTING SENSITIVITY PARAMETER VALUE FOR SUBSTRATE DEFECT INSPECTION, AND NON-TRANSITORY STORAGE MEDIUM

(71) Applicant: Tokyo Electron Limited, Tokyo (JP)

(72) Inventors: Yasuhiro Kitada, Sapporo (JP); Izumi Hasegawa, Koshi (JP); Hiroshi Tomita, Koshi (JP); Kousuke Nakayama, Koshi (JP); Tadashi Nishiyama, Koshi (JP)

(73) Assignee: Tokyo Electron Limited, Tokyo (JP)

( * ) Notice: Subject to any disclaimer, the term of this patent is extended or adjusted under 35 U.S.C. 154(b) by 2 days.

(21) Appl. No.: 15/634,189

(22) Filed: Jun. 27, 2017

(65) Prior Publication Data

US 2018/0005370 A1 Jan. 4, 2018

(30) Foreign Application Priority Data

Jun. 30, 2016 (JP) .................................. 2016-130593

(51) Int. Cl.
| | | |
|---|---|---|
| *G06K 9/00* | (2006.01) | |
| *G06T 7/00* | (2017.01) | |
| *G06T 7/90* | (2017.01) | |
| *G01N 21/95* | (2006.01) | |

(52) U.S. Cl.
CPC ....... *G06T 7/0008* (2013.01); *G01N 21/9501* (2013.01); *G06T 7/90* (2017.01); *G01N 2201/12* (2013.01); *G06T 2207/30148* (2013.01)

(58) Field of Classification Search
CPC ....... H01L 22/12; G01N 21/9501; G03F 1/38; G03F 1/42; G03F 1/44; G06T 7/70; G06T 2207/30148; G06T 2207/30164; B23Q 17/2452; B23Q 17/2457; B23Q 17/2471; B23Q 17/249; G05B 2219/31432; G05B 2219/36251; G05B 2219/37555; G05B 2219/37578; G05B 2219/50064

See application file for complete search history.

(56) References Cited

U.S. PATENT DOCUMENTS

2012/0092656 A1* 4/2012 Nakao ................ G01N 21/8851
356/237.3

FOREIGN PATENT DOCUMENTS

JP 2014-115140 A 6/2014

* cited by examiner

*Primary Examiner* — Duy M Dang
(74) *Attorney, Agent, or Firm* — Posz Law Group, PLC

(57) ABSTRACT

A method of adjusting a sensitivity parameter value for substrate defect inspection used in a substrate defect inspection apparatus compares, for each pixel value of a selected virtual inspection substrate, using reference pixel data to be used after adjustment, the deviation amount from an allowable range corresponding to the position thereof and the sensitivity parameter value before the adjustment when each pixel value is deviated from the allowable range, and updates the deviation amount as a new sensitivity parameter value when the deviation amount exceeds the sensitivity parameter value and a difference between the deviation amount and the sensitivity parameter value is equal to or less than a threshold value.

9 Claims, 13 Drawing Sheets

FIG.7

| WAFER NUMBER | RGB | ZERNIKE COEFFICIENT (FEATURE AMOUNT) Z1 |
|---|---|---|
| 1 | R | 199.072 |
| | G | 190.2805 |
| | B | 128.7317 |
| 2 | R | 186.684 |
| | G | 172.689 |
| | B | 158.2237 |
| 3 | R | 198.696 |
| | G | 191.4602 |
| | B | 135.4903 |
| ... | ... | ... |
| 100 | R | 189.1831 |
| | G | 189.9453 |
| | B | 125.9754 |

FIG.11

| ZERNIKE COEFFICIENT (FEATURE AMOUNT) | RGB | WAFER NUMBER | | | | |
|---|---|---|---|---|---|---|
| | | 1 | 2 | 3 | ... | 1000 |
| Z1 | R | 199.072 | 186.684 | 198.696 | ... | 189.1831 |
| | G | 190.2805 | 172.689 | 191.4602 | ... | 189.9453 |
| | B | 128.7317 | 158.2237 | 135.4903 | ... | 125.9754 |

→ R-Z1 GROUP

SUBSTRATE DEFECT INSPECTION APPARATUS, METHOD OF ADJUSTING SENSITIVITY PARAMETER VALUE FOR SUBSTRATE DEFECT INSPECTION, AND NON-TRANSITORY STORAGE MEDIUM

CROSS REFERENCE TO RELATED APPLICATION

This application is based upon and claims the benefit of priority of the prior Japanese Patent Application No. 2016-130593, filed in Japan on Jun. 30, 2016, the entire contents of which are incorporated herein by reference.

BACKGROUND OF THE INVENTION

1. Field of the Invention

The present invention relates to a defect inspection apparatus for determining a defect of a substrate using image data obtained by picking up an image of the substrate, a method of adjusting a sensitivity parameter value for substrate defect inspection, and a non-transitory storage medium storing a computer program used for the defect inspection apparatus.

2. Description of the Related Art

In a photolithography process being one of manufacturing processes of a semiconductor device, formation of a resist film by applying a resist onto the front surface of a semiconductor wafer (hereinafter, described as a wafer) being a substrate, and exposure and development of the resist film are performed in sequence to form a resist pattern. At each portion within the plane of the wafer on which the resist pattern is formed, defect inspection for determining the presence or absence of a defect may be performed in some cases. This defect inspection is performed based on image data obtained by picking up an image of a wafer being an inspection object, previously prepared reference image data, and a plurality of parameters used in determination whether or not a portion is a defect.

A portion is not actually a defect but is sometimes determined to be a defect in the above defect inspection, and this portion is called a false defect. The above parameters are required to be set to suppress occurrence of the false defect. Further, when forming the above resist film, the parameters sometimes need to be set again for the purpose of manufacturing a new semiconductor device or improving the yield, for example, when change of various processing conditions such as change of material of the resist to be used is performed or when the brightness of a light source of illumination used at the time of inspection is changed.

However, as for the above parameter, many parameters exist, and therefore the operator of an apparatus comes to repeat operations of changing the parameters and checking the influence of the change on the inspection many times, requiring a lot of labor and time as a result of the trial and error. Further, since the combination of appropriate parameter values is not one, set parameter values sometimes differ depending on the level of skill of the operator. In other words, the accuracy of the inspection is influenced by the level of skill of the operator setting the parameter values, thus possibly failing to sufficiently prevent the false defect.

In this regard, Japanese Patent Application Publication No. 2014-115140 discloses a method of creating reference image data, but does not describe a method of setting the above parameter value, which is insufficient to solve this problem.

SUMMARY OF THE INVENTION

The present invention has been made to solve the problem, and its object is to enable automatic adjustment of a parameter value used at the time of defect inspection on a substrate, and decrease the detection frequency of a false defect at the time of the defect inspection on a substrate.

A substrate defect inspection apparatus according to one aspect of the present invention is configured to compare, for each pixel value of image data obtained by picking up an image of an entire front surface of a substrate being an inspection object, using reference pixel data made by associating each position and an allowable range of the pixel value, a deviation amount from the allowable range and a sensitivity parameter value being an allowable deviation amount when each pixel value is deviated from the allowable range corresponding to the position thereof, and determine the substrate to be a defective substrate when the deviation amount exceeds the sensitivity parameter value.

The substrate defect inspection apparatus includes: a reference pixel data creation unit that creates, at adjustment time of the sensitivity parameter value, reference pixel data to be used after the adjustment; an adjustment unit for the sensitivity parameter value for adjusting the sensitivity parameter value; and a virtual inspection substrate selection unit that selects a plurality of virtual inspection substrates which are used for adjusting the sensitivity parameter value and on which virtual inspection being inspection for adjusting the sensitivity parameter is to be performed by comparison with the reference pixel data, from among a plurality of substrates inspected earlier than the adjustment time of the sensitivity parameter value, Further, the adjustment unit for the sensitivity parameter value is configured to execute: a first step of comparing, for each pixel value of the selected virtual inspection substrate, using the reference pixel data to be used after the adjustment, the deviation amount from the allowable range and the sensitivity parameter value before the adjustment when each pixel value is deviated from the allowable range corresponding to the position thereof; a second step of updating the deviation amount as a new sensitivity parameter value when the deviation amount exceeds the sensitivity parameter value and a difference between the deviation amount and the sensitivity parameter value is equal to or less than a threshold value; and a third step of performing the first step and the second step in sequence on image data on the plurality of substrates inspected earlier, and, when the sensitivity parameter value being an object to be compared with the deviation amount has been updated, storing in a storage unit a finally updated sensitivity parameter value as the sensitivity parameter after the adjustment, using the updated sensitivity parameter value.

One aspect of the present invention according to another viewpoint is a method of adjusting a sensitivity parameter value for substrate defect inspection used in a substrate defect inspection apparatus, configured to compare, for each pixel value of image data obtained by picking up an image of an entire front surface of a substrate being an inspection object, using reference pixel data made by associating each position and an allowable range of the pixel value, a deviation amount from the allowable range and a sensitivity parameter value being an allowable deviation amount when each pixel value is deviated from the allowable range corresponding to the position thereof, and determine the substrate to be a defective substrate when the deviation amount exceeds the sensitivity parameter value, the method including:

a step of creating, at adjustment time of the sensitivity parameter value, reference pixel data to be used after the adjustment;

a step of adjusting the sensitivity parameter value;

a step of selecting a virtual inspection substrate which is used for adjusting the sensitivity parameter value and on which virtual inspection is to be performed by comparison with the reference pixel data, from among a plurality of substrates inspected earlier than the adjustment time of the sensitivity parameter value, a step of comparing, for each pixel value of the selected virtual inspection substrate, using the reference pixel data to be used after the adjustment, the deviation amount from the allowable range and the sensitivity parameter value before the adjustment when each pixel value is deviated from the allowable range corresponding to the position thereof;

a step of updating the deviation amount as a new sensitivity parameter value when the deviation amount exceeds the sensitivity parameter value and a difference between the deviation amount and the sensitivity parameter value is equal to or less than a threshold value; and a step of performing the above steps in sequence on image data on the plurality of substrates inspected earlier, and, when the sensitivity parameter value being an object to be compared with the deviation amount has been updated, storing in a storage unit a finally updated sensitivity parameter value as the sensitivity parameter after the adjustment, using the updated sensitivity parameter value.

One aspect of the present invention according to still another viewpoint is a non-transitory storage medium storing a computer program to execute a method of adjusting a sensitivity parameter value for substrate defect inspection in a substrate defect inspection apparatus, the method of adjusting a sensitivity parameter value for substrate defect inspection, configured to compare, for each pixel value of image data obtained by picking up an image of an entire front surface of a substrate being an inspection object, using reference pixel data made by associating each position and an allowable range of the pixel value, a deviation amount from the allowable range and a sensitivity parameter value being an allowable deviation amount when each pixel value is deviated from the allowable range corresponding to the position thereof, and determine the substrate to be a defective substrate when the deviation amount exceeds the sensitivity parameter value, including:

a step of creating, at adjustment time of the sensitivity parameter value, reference pixel data to be used after the adjustment;

a step of adjusting the sensitivity parameter value;

a step of selecting a virtual inspection substrate which is used for adjusting the sensitivity parameter value and on which virtual inspection is to be performed by comparison with the reference pixel data, from among a plurality of substrates inspected earlier than the adjustment time of the sensitivity parameter value, a step of comparing, for each pixel value of the selected virtual inspection substrate, using the reference pixel data to be used after the adjustment, the deviation amount from the allowable range and the sensitivity parameter value before the adjustment when each pixel value is deviated from the allowable range corresponding to the position thereof;

a step of updating the deviation amount as a new sensitivity parameter value when the deviation amount exceeds the sensitivity parameter value and a difference between the deviation amount and the sensitivity parameter value is equal to or less than a threshold value; and a step of performing the above steps in sequence on image data on the plurality of substrates inspected earlier, and, when the sensitivity parameter value being an object to be compared with the deviation amount has been updated, storing in a storage unit a finally updated sensitivity parameter value as the sensitivity parameter after the adjustment, using the updated sensitivity parameter value.

The present invention compares the image data obtained by picking up an image of the entire front surface of the substrate and the reference pixel data and automatically adjusts the sensitivity parameter value for determining whether or not the substrate is defective. More specifically, the present invention selects a plurality of virtual inspection substrates from among a plurality of substrates inspected earlier than the adjustment time of the sensitivity parameter value, performs virtual inspection by comparing new reference pixel data after the adjustment of the sensitivity parameter and the image data, and eases the sensitivity parameter value so as to prevent, when a certain substrate is determined to be a false defective substrate, the substrate from being determined to be a defective substrate in actual inspection.

The present invention further performs, in sequence on the plurality of selected virtual inspection substrates, the above operations, namely, selecting a plurality of virtual inspection substrates from among a plurality of substrates inspected earlier than the adjustment time of the sensitivity parameter value, performing virtual inspection by comparing new reference pixel data after the adjustment of the sensitivity parameter and the image data, and easing the sensitivity parameter value as described above, and uses a finally acquired sensitivity parameter value as a new sensitivity parameter value. Accordingly, the burden on the operator who performs the adjustment of the sensitivity parameter value by trial and error is eliminated, and stable substrate defect inspection can also be realized.

BRIEF DESCRIPTION OF THE DRAWINGS

FIG. 7 is a chart illustrating an example of acquired feature amounts of wafers;

FIG. 11 is a chart illustrating an example of the acquired feature amounts of wafers;

DETAILED DESCRIPTION OF THE INVENTION

Figure 1:
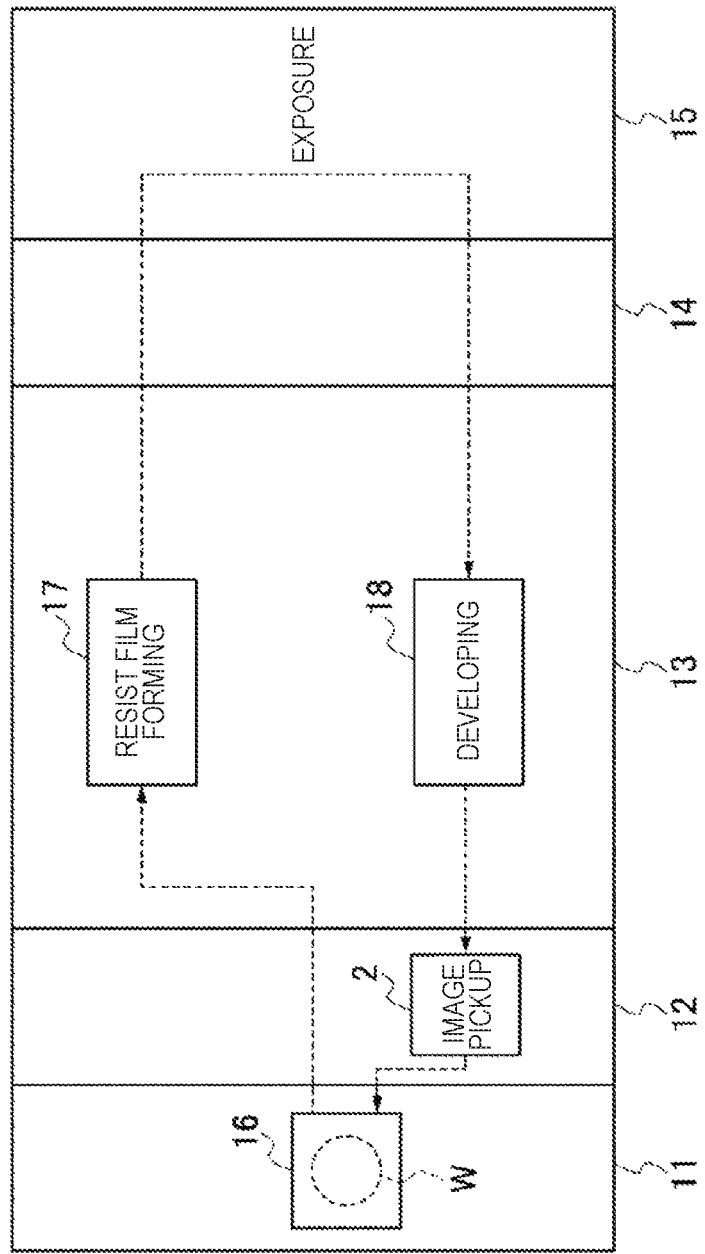
FIG. 1 is an explanatory view illustrating the outline of the entire configuration of a coating and developing apparatus to which the present invention is applied.

A coating and developing apparatus 1 being one embodiment to which the present invention is applied will be explained referring to a schematic plan view in FIG. 1. The coating and developing apparatus 1 is composed of a carrier block 11, an intermediate block 12, a treatment block 13, and an interface block 14 which are connected in this order in a linear arrangement in a horizontal direction. To the interface block 14, an exposure apparatus 15 is connected. A carrier 16 in which wafers W being substrates are stored is transferred to and mounted on the carrier block 11 by a not-illustrated transfer mechanism. In the treatment block 13, a resist film forming module 17 that supplies a resist solution to the front surface of the wafer W to form a resist film, and a developing module 18 that supplies a developing solution to the resist film exposed along a predetermined pattern in the exposure apparatus 15 to form a resist pattern, are provided. In the intermediate block 12, an image pickup module 2 that picks up an image of the entire front surface of the developed wafer W is illustrated. Note that the entire front surface of the wafer W only needs to be the entire front surface of a region where semiconductor devices are to be formed.

Each of the blocks 11 to 14 has a not-illustrated transfer mechanism for the wafer W. The wafer W stored in the carrier 16 is transferred by the transfer mechanisms in the order of the intermediate block 12, the resist film forming module 17, the interface block 14, the exposure apparatus 15, the interface block 14, the developing module 18, and the image pickup module 2, and then returned to the carrier 16. Dashed line arrows in FIG. 1 indicate a transfer route of the wafer W. Through thus transfer of the wafer W, formation of the resist pattern on the front surface of the wafer W and image pickup of the entire front surface of the wafer W are performed. Image data obtained by the image pickup is used for inspecting the presence or absence of abnormality within the plane of the wafer W. Note that the image data is data containing information on pixel values of R (red), G (green), B (blue) being three primary colors for a pixel at each position in the image.

In this coating and developing apparatus 1, the above inspection, namely, inspection of determining whether there is or not an actual abnormality on the wafer W and inspection for adjusting later-explained sensitivity parameters used for the former inspection are performed. Hereinafter, the inspection of determining whether or not there is an actual abnormality on the wafer W is described as actual inspection, and the inspection for adjusting sensitivity parameters is described as virtual inspection. Note that the inspection and the parameters described in the section of Related Art correspond to the actual inspection and the sensitivity parameters, respectively.

The above actual inspection on the wafer W will be explained. The actual inspection is performed by comparing pre-created reference image data on the wafer W with image data obtained from the wafer W being an inspection object. The reference image data on the wafer W (reference pixel data) is data made by associating the position of a pixel with an allowable range of the pixel value for each pixel of the image of the wafer for each R, G, B. Besides, comparing the reference image data on the wafer W with the image data on the wafer W being an inspection object, referred to here, means comparing the pixel values of each R, G, B regarding the pixels at the same position with each other between the reference image data and the image data on the wafer W being an inspection object, and means, in more detail, acquiring a difference value between the pixel value in the allowable range of the reference image data and the pixel value of the image data on the inspection object wafer W. In other words, the difference value is a deviation amount of the pixel value of the image data on the inspection object wafer W from the allowable range. To be more precise, when the pixel value of the image data on the inspection object wafer W exceeds an upper limit value of the allowable range, the difference from the upper limit value is the deviation amount, whereas when the pixel value of the image data on the inspection object wafer W exceeds a lower limit value of the allowable range, the difference from the lower limit value is the deviation amount.

When the deviation amount of each R, G, B is 0 in pixels at all positions, the inspection object wafer W is determined to have no defect. On the other hand, when any of the deviation amounts of R, G, B is not 0 in a pixel at any position, such a deviation amount not being 0 is compared with the sensitivity parameter value being an allowable deviation amount set for each R, G, B. When the deviation amount exceeds the sensitivity parameter value as a result of the comparison, it is determined that a defect has occurred at a position corresponding to this pixel in the inspection object wafer W and the inspection object wafer W is a defective wafer W having a defect. When the deviation amount does not exceed this sensitivity parameter value, it is determined that the wafer W is not a defective wafer W.

Figure 2:
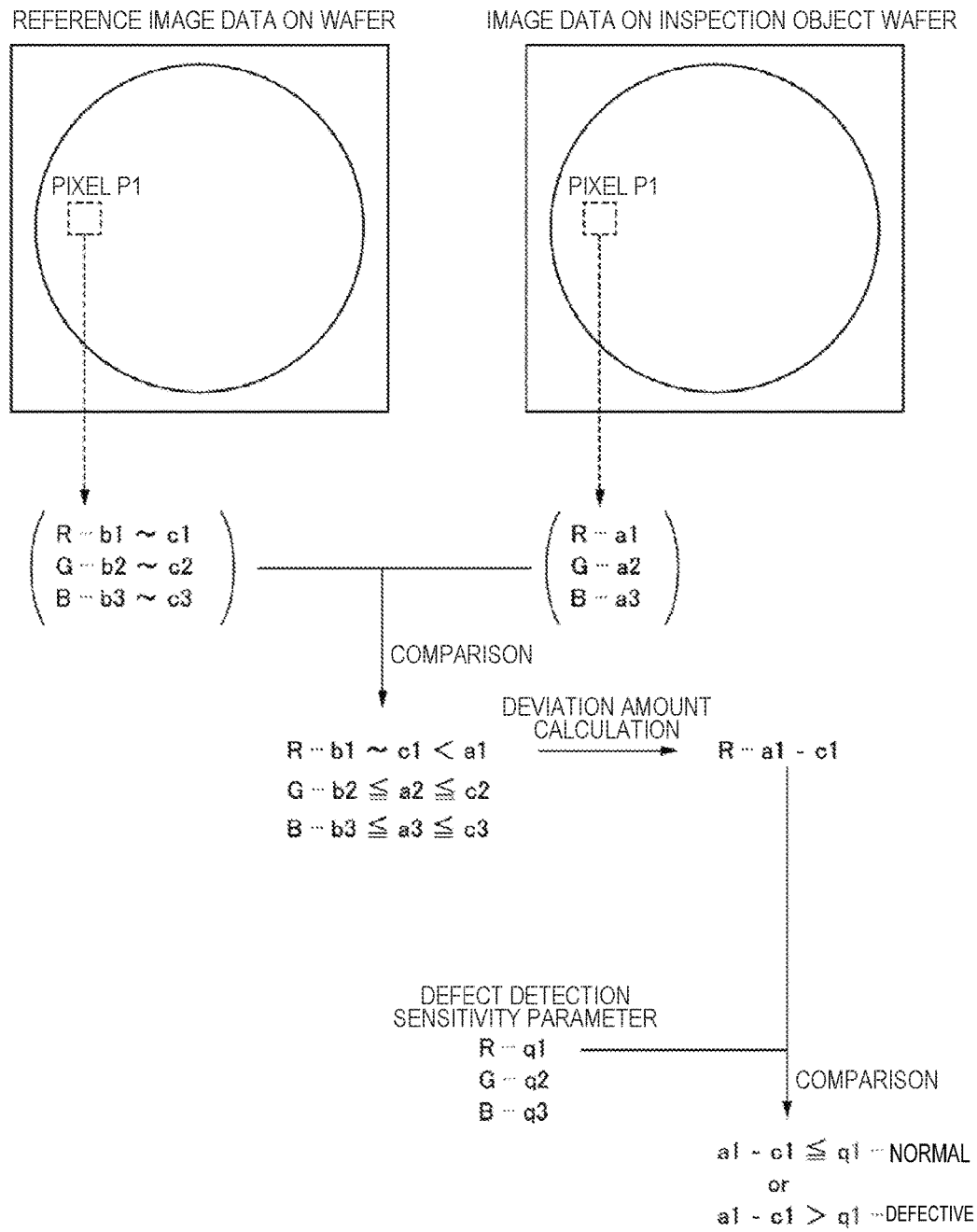
FIG. 2 is an explanatory view of the outline of actual inspection executed in the coating and developing apparatus.

FIG. 2 schematically illustrates the procedure of the above actual inspection, and for the image data on the inspection object wafer W and the reference image data on the wafer W, an arbitrary pixel at the same position is set as P1 in each data. R, G, B in the pixel P1 of the inspection object wafer W are a1, a2, a3 respectively, and allowable ranges of R, G, B in the pixel P1 of the reference image data are b1 to c1, b2 to c2, b3 to c3 respectively. In this example, it is assumed that the pixel value of the inspection object wafer W is not included in the allowable range only regarding R of R, G, B. Accordingly, in this case, b1 to c1<a1 and a deviation amount a1−c1 does not become 0.

To be more precise, the allowable ranges of R, G, B are b1 to c1, b2, to c2, b3 to c3 respectively. Here, b1, b2, b3 are allowable lower limit values, and c1, c2, c3 are allowable upper limit values. When it is assumed that the pixel value of the inspection object wafer W is not included in the allowable range only regarding R of R, G, B, a1<b1 or a1>c1, and therefore in such case each absolute value of a1−b1 or a1−c1 being the deviation amount does not become zero.

Further, for example, when it is assumed that the sensitivity parameters for R, G, B are set as q1, q2, q3 respectively, the deviation amount a1−c1 is compared with the sensitivity parameter q1 for R, and when q1<a1−c1, a portion corresponding to the pixel P1 is determined to be a defect, whereas when q1≥a1−c1, the portion corresponding to the pixel P1 is determined to be not a defect. Note that the comparison between the image data on the inspection object wafer W and the reference image data on the wafer W is illustrated to be performed only at the pixel P1 so as to prevent complication of the drawing, but this comparison is performed for each pixel within the plane of the wafer W. Further, each comparison, each determination, and calculation of the deviation amount in the above explanation for the actual inspection are executed by a later-explained computer.

For a supplementary explanation about the above sensitivity parameters, for example, four kinds of sensitivity parameters D1 to D4 are set for each R, G, B as the above sensitivity parameters, and set so that any one or a plurality of the sensitivity parameters D1 to D4 are used according to the position of the pixel for which the deviation amount is calculated. In other words, it is assumed that the above defect determinations using the sensitivity parameters D1, D2, D3, D4 respectively are defect determination modes 1, 2, 3, 4, a region where the defect determination is performed within plane of the wafer W is set for each of the defect determination modes 1 to 4. For example, one of the sensitivity parameters D1 to D4 is applied to the defect determination at a central portion of the wafer W, and another one of the sensitivity parameters D1 to D4 is applied to the defect determination at a peripheral portion of the wafer W.

In the coating and developing apparatus 1, updating of the reference image data on the wafer W and the sensitivity parameters D1 to D4 is automatically performed by the computer. The updating of the reference image data on the wafer W and the sensitivity parameters D1 to D4 is executed using many pieces of image data on the wafers W which have been obtained in advance by image pickup in the image pickup module 2 before performing the updating. Schematically explaining details, image data that is clearly considered to contain a defect is excluded from the many pieces of obtained image data, and reference image data on the wafer W is newly created from remaining many pieces of image data after the exclusion is performed as explained above.

Then, an inspection for presence or absence of a defect is performed using the newly created reference image data on the wafer W, for each of remaining many pieces of image data on the wafers W after the above-explained exclusion is performed. This inspection is the above virtual inspection, and when the wafer W is determined to have no defect in virtual inspection, the sensitivity parameters D1 to D4 are updated to become such values that if the wafer W is subjected to actual inspection, the wafer W is not determined to be a defective wafer W. Timing when the updating of the reference image data on the wafer W and the sensitivity parameters D1 to D4 is decided based on the feature amounts of the wafer W being the parameters acquired from each of many pieces of image data on the wafers W which have been obtained before the updating is performed. More specifically, whether or not the acquired feature amount is deviated from an upper threshold value or a lower threshold value which are preset is determined by the computer, and the timing for updating is decided based on the result of the determination.

As the above feature amounts (feature points) of the wafer W, Zernike coefficients $Zi$ (i is an integer of 1 or more) expressed by decomposing a planar distribution Z of the pixel values within the wafer plane by the Zernike function using the Zernike polynomial for each R, G, B are used. The Zernike coefficients $Zi$ individually indicate distribution characteristics of the pixel values within the plane of the wafer W respectively. In the following explanation, it is assumed that, for example, four Z1 to Z4 of the Zernike coefficients $Zi$ are used as the feature amounts of the wafer W, but the Zernike coefficients $Zi$ to be used as the feature amounts in this manner are not particularly limited. Accordingly, for example, Zernike coefficients $Zi$ other than Z1 to Z4 can be used as the feature amounts of the wafer W, and the number of Zernike coefficients $Zi$ to be used is not limited to four.

A method of acquiring the Zernike coefficients $Zi$ is explained. The Zernike coefficients $Zi$ are acquired using the Zernike polynomial as explained above. The Zernike polynomial is a function of complex variable mainly used in the optical field and has two degrees (n, m). The Zernike polynomial is also a function on a unit circle having a radius of 1 and has arguments (r, θ) of polar coordinates. The Zernike polynomial is used to analyze, for example, the aberration component of a lens in the optical field, so that the aberration component based on each independent wavefront, for example, the shape of a mount, a saddle or the like can be recognized by decomposing wavefront aberration by using the Zernike polynomial.

Figure 3:
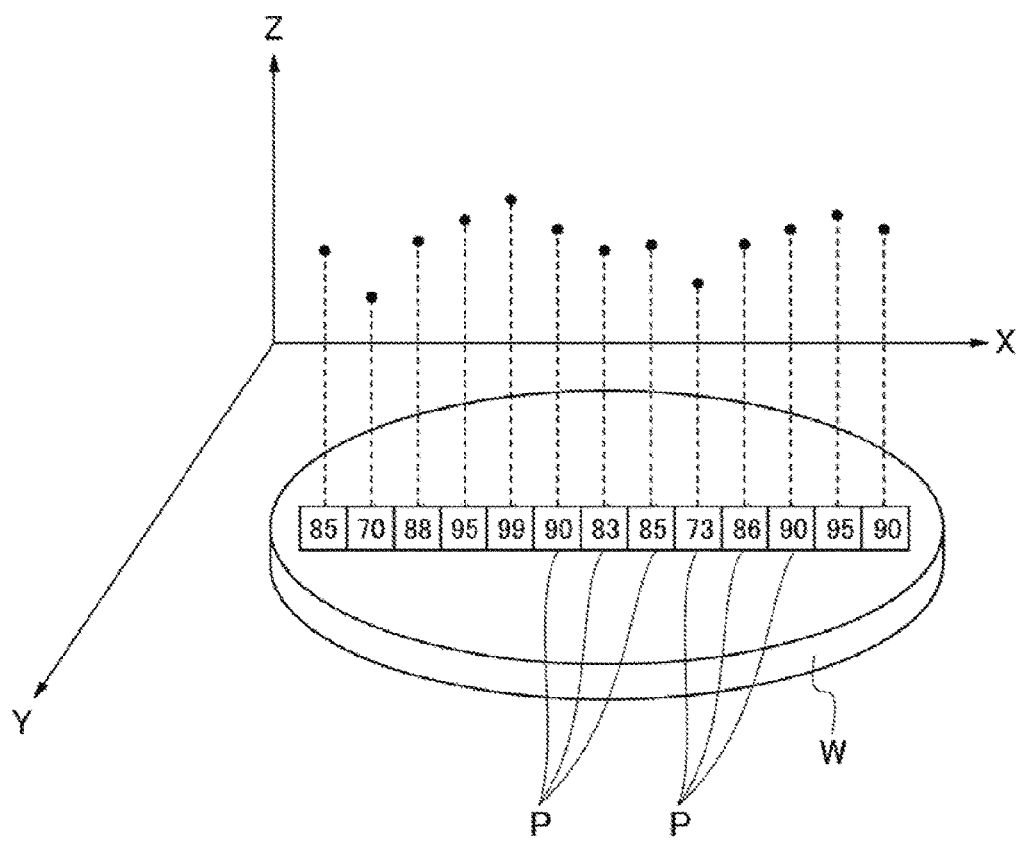
FIG. 3 is an explanatory view of a front surface of a wafer whose image is picked up.

Hereinafter, explanation will be made referring to FIG. 3. FIG. 3 expresses the planar distribution Z of the pixel values of pixels P within the plane of the wafer W, in which the numeric value indicated inside each pixel P illustrated by a rectangle represents the pixel value of the pixel P. For easy explanation, only pixels P in one line along an X-axis direction are illustrated in FIG. 3. When applying the Zernike polynomial to the planar distribution Z of the pixel values, the pixel values of the pixels P are expressed in the height direction on the plane of the wafer W (in a Z-direction positive direction in FIG. 3). As a result, the planar distribution of the pixel values of the pixels P can be grasped as a curve in a predetermined shape drawn in three dimensions. Further, the pixels values of all the pixels P within the plane of the wafer W are similarly expressed in the height direction on the plane of the wafer W, whereby the distribution of the pixel values within the plane of the wafer W can be grasped as a circular wavefront in three dimensions. Grasping the distribution as the wavefront in three dimensions in this manner makes it possible to apply the Zernike polynomial, and to decompose the planar distribution Z of the pixel values within the plane of the wafer, for example, into a plurality of pixel value distribution components $Zi$ such as gradient components in the right, left, top and bottom directions within the plane of the wafer, curvature components curved in a convex shape or a concave shape and so on through the use of the Zernike polynomial. The magnitude of each of the pixel value distribution components $Zi$ can be expressed by the Zernike coefficient $Zi$.

The Zernike coefficient representing each of the pixel value distribution components $Zi$ can be concretely expressed by using polar coordinate arguments (r, θ) and degrees (n, m). The Zernike coefficients of a first term to a ninth term are listed below as examples.

Z1, n=0, m=0
(1)
Z2, n=1, m=1
(r·cos θ)
Z3, n=0, m=−1
(r·sin θ)
Z4, n=2, m=0
($2r^2-1$)
Z5, n=2, m=2
($r^2 \cdot \cos 2θ$)
Z6, n=2, m=−2
($r^2 \cdot \sin 2θ$)
Z7, n=3, m=1
(($3r^3-2r$)·cos θ)
Z8, n=3, m=−1
(($3r^3-2r$)·sin θ)
Z9, n=4, m=0
($6r^4-6r^2+1$)

For example, the Zernike coefficient Z1 being the Zernike coefficient of the first term means the average value of the pixel values within the plane of the wafer, the second Zernike coefficient Z2 means the gradient component in the right-left direction of the pixel values within the plane of the wafer, the third Zernike coefficient Z3 means the gradient component in the forward-backward direction (a direction perpendicular to the direction of the gradient of the second Zernike coefficient Z2) of the pixel values within the plane of the wafer, and the fourth Zernike coefficient Z4 means the curvature component of the pixel values with the center of the wafer as the origin.

Figure 4:
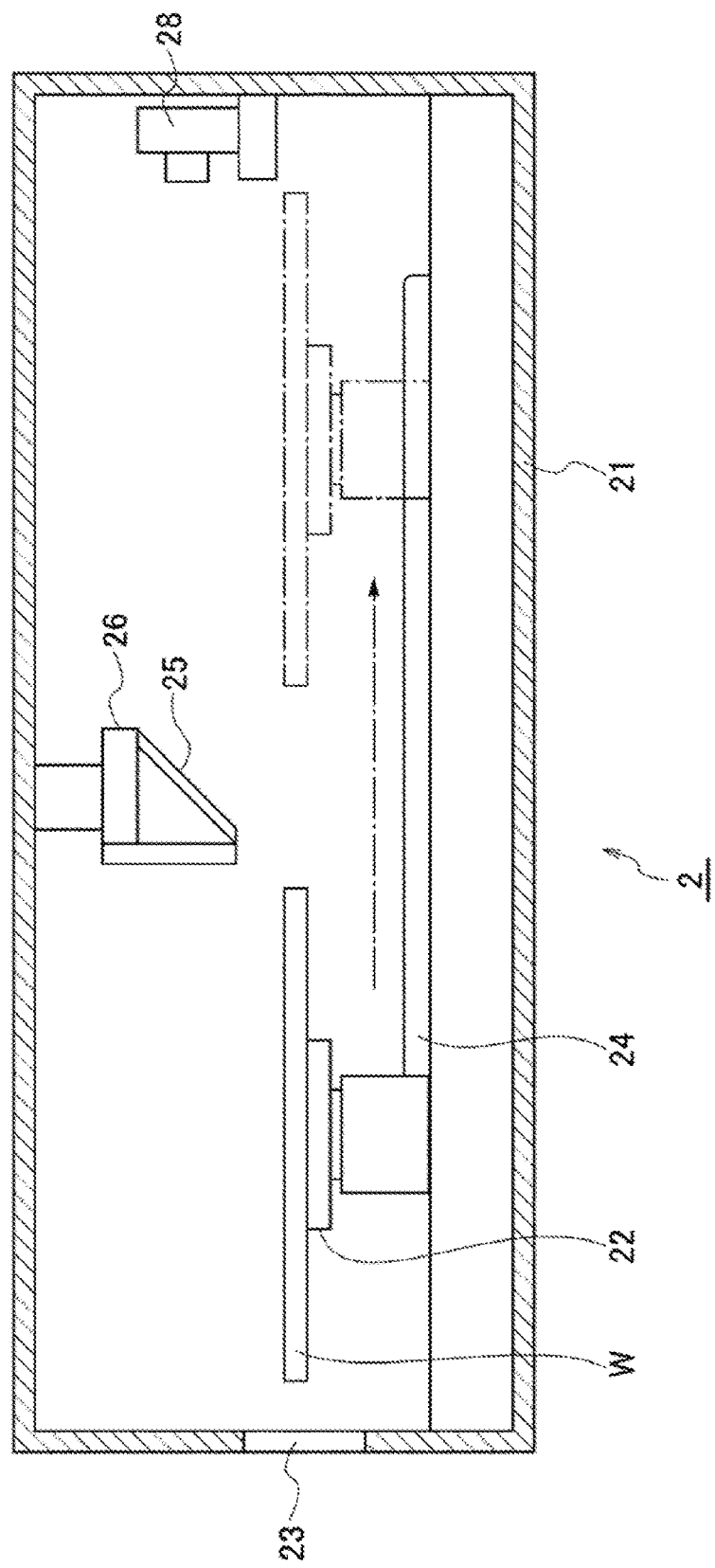
FIG. 4 is an explanatory view schematically illustrating a cross-section of a side surface of an image pickup module provided in the coating and developing apparatus, to obtain the image of the front surface of the wafer.

Returning to the explanation of the configuration of the coating and developing apparatus 1, the above image pickup module 2 will be explained referring to a side surface cross-sectional view in FIG. 4. The image pickup module 2 includes a housing 21, and a mounting table 22 that sucks a central portion on the rear surface side of the wafer W to horizontally hold the wafer W thereon which is provided in the housing 21. In the drawing, a numeral 23 denotes a transfer port for the wafer W opened in the side of the housing 21. When it is assumed that the side where the transfer port 23 is opened in the housing 21 is the near side, the mounting table 22 is configured to be movable in the horizontal direction between the near side and the distant side. In the drawing, a numeral 24 denotes a guide for the horizontal movement of the mounting table 22 and extends from the near side to the distant side.

On the guide 24, a horizontally long half mirror 25 extending to right and left in the housing 21 is provided, and the half mirror 25 is provided obliquely in a side view with respect to the extending direction of the guide 24. Further, above the half mirror 25, a lighting 26 that irradiates light downward via the half mirror 25 is provided. On the distant side of the half mirror 25, a camera 28 is provided. Lighting from the lighting 26 passes through the half mirror 25 and is applied to an irradiation region below the half mirror 25. Then, reflected light from an object in the irradiation region is reflected by the half mirror 25 and captured into the camera 28. In short, the camera 28 can pick up an image of the object located below the half mirror 25. Then, while the wafer W is moving from the near side to the distant side below the half mirror 25 along the guide 24, the camera 28 intermittently performs image pickup to pick up an image of the entire front surface of the wafer W and thereby can create the image data.

Figure 5:
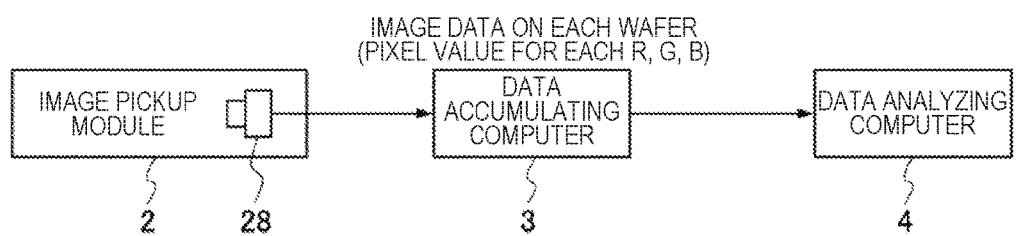
FIG. 5 is an explanatory view illustrating the configuration of a defect inspection system for wafer, provided in the coating and developing apparatus.

The camera 28 of the image pickup module 2 is connected to a data accumulating computer 3 as illustrated in FIG. 5, and transmits the obtained image data on each wafer W to the data accumulating computer 3. The data accumulating computer 3 stores and accumulates the received image data in a memory included in the computer 3. The data accumulating computer 3 is connected to a data analyzing computer 4. The data analyzing computer 4 is a computer for updating the above reference image data on the wafer W and the sensitivity parameters D1 to D4 using the image data on the wafer W accumulated in the data accumulating computer 3. The image pickup module 2, the data accumulating computer 3, and the data analyzing computer 4 constitute the substrate defect inspection apparatus.

Figure 6:
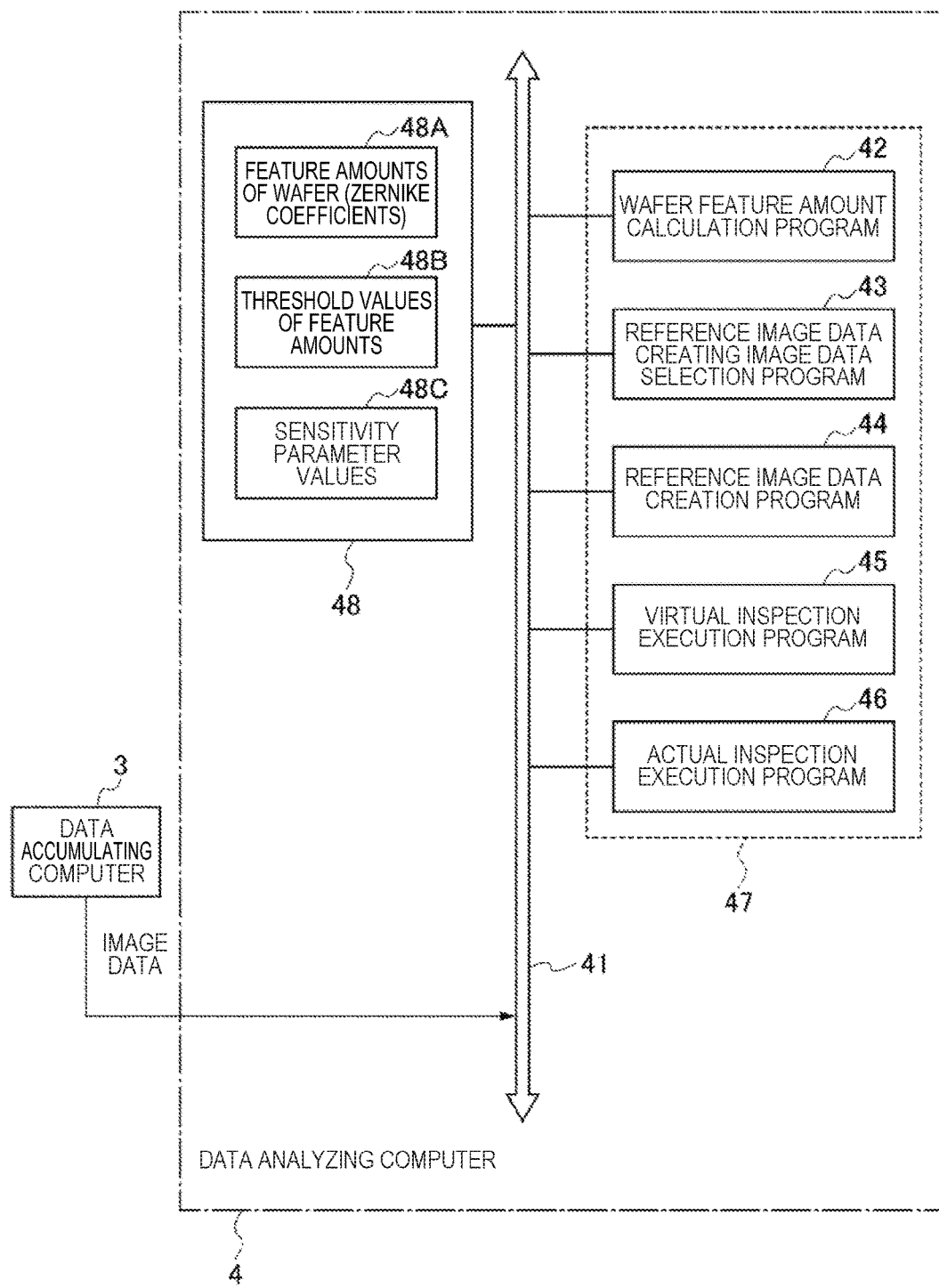
FIG. 6 is a block diagram illustrating a data analyzing computer constituting the defect inspection system.

Subsequently, the configuration of the data analyzing computer 4 will be explained using FIG. 6. In the drawing, a numeral 41 denotes a bus, and a program storage unit 47 that stores programs 42 to 46 and a memory 48 are connected to the bus 41. Further, the data accumulating computer 3 is also connected to the bus 41 and is configured to be able to transmit the image data on the wafer W to the data analyzing computer 4.

The program 42 is a wafer feature amount calculation program forming a monitoring threshold value creation unit that calculates the above Zernike coefficients Zi (Z1 to Z4) being the feature amounts using the image data on the wafers W from the data accumulating computer 3. The program 42 is configured also as a monitoring unit that decides the timing for updating the above sensitivity parameters D by monitoring whether or not the Zernike coefficients Zi are deviated from threshold values stored in the memory 48.

The program 43 is a reference image data creating image data selection program for selecting the image data for creating the reference image data on the wafer W from the image data on the wafers W accumulated in the data accumulating computer 3. The program 44 is a reference image data creation program for creating the reference image data on the wafer W using the image data selected by the program 43, and is configured as a reference pixel data creation unit.

The program 45 is a virtual inspection execution program for selecting the image data on which virtual inspection is to be executed, from the image data on the wafers W accumulated in the data accumulating computer 3 and executing virtual inspection. By the program 45, the updating of the sensitivity parameters D and updating of the threshold values of the Zernike coefficients Zi are also performed. The program 45 is configured as an adjustment unit for the parameter values. The program 46 is actual inspection execution program for executing the already-explained actual inspection.

The programs 42 to 46 are stored in the program storage unit 47, for example, in a state of being accommodated in a transitory or non-transitory storage medium such as a hard disk, compact disk, magneto-optical disk or memory card. In addition, a processing step group is installed in the programs 42 to 46 so as to enable execution of processing such as the already-explained actual inspection, the later-explained adjustment of the sensitivity parameters and so on.

The memory 48 being a storage unit includes storage regions 48A to 48C. In the storage region 48A, the Zernike coefficients Zi of the wafer W for each R, G, B acquired from the image data on each wafer W explained with FIG. 3 are stored in association with the wafer W whose image data has been obtained. In FIG. 7, the acquired Zernike coefficients Z1 acquired for 100 wafers W (numbers of 1 to 100 are attached thereto for convenience) whose image data have been recently obtained are illustrated as examples. Note that the Zernike coefficients Z2 to Z4 other than Z1 are also stored in the storage region 48A as with Z1 but illustration of them in the drawing is omitted.

In the storage region 48B, the upper limit threshold value and the lower limit threshold value being the allowable range about the above Zernike coefficient are stored. The upper limit threshold value and the lower limit threshold value are set for each of the Zernike coefficients Zi of the wafer W for each R, G, B. When the updating of the sensitivity parameter values and the reference image data on the wafer W is performed as explained above, the upper limit threshold values and the lower limit threshold values stored in the storage region 48B are reset. In the storage region 48C, the sensitivity parameters D1 to D4 are stored for each R, G, B.

Figure 8:
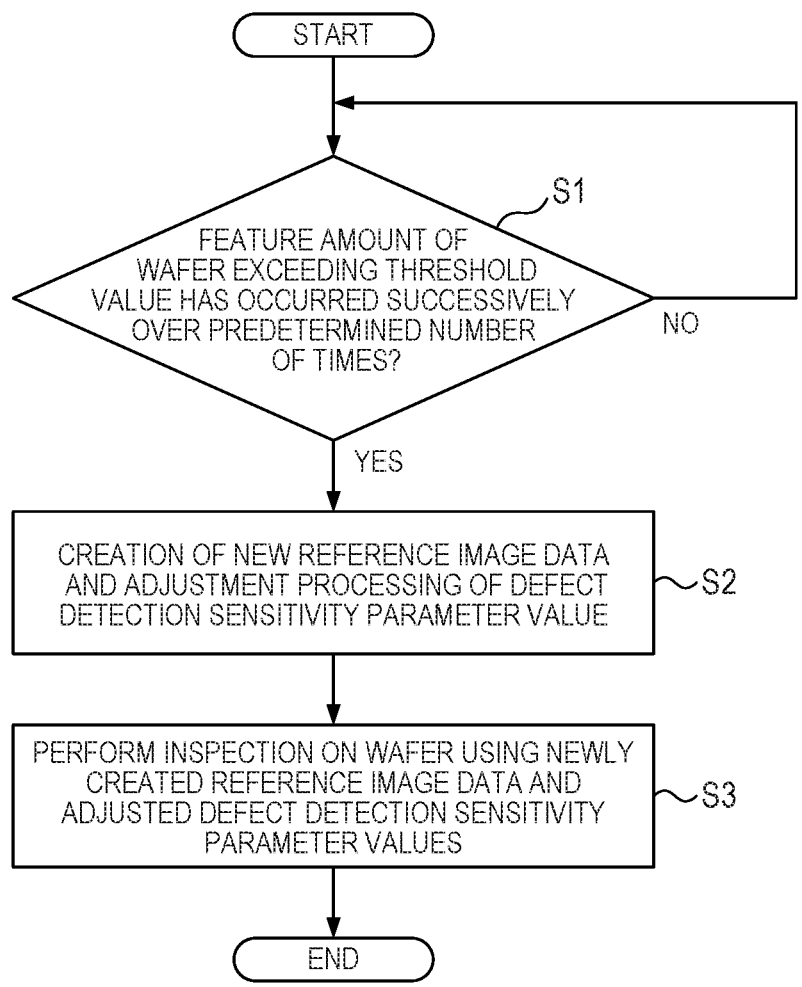
FIG. 8 is a flowchart of defect inspection on a wafer.

Subsequently, the procedure of processing performed by the above coating and developing apparatus 1, data accumulating computer 3, and data analyzing computer 4 will be explained referring to a flowchart in FIG. 8. As explained with FIG. 1, the wafers W are transferred into the coating and developing apparatus 1, image data (image data on the inspection object wafers W) are obtained by picking up images of the wafers W on which the resist patterns have been formed, and the image data are transmitted in sequence to the data accumulating computer 3. And the image data are transmitted from the data accumulating computer 3 to the data analyzing computer 4, and compared with the wafer reference image data as explained with FIG. 2 to perform actual inspection for the wafers W corresponding to the image data. Further, in parallel with the actual inspection, calculation of the Zernike coefficients Z1 to Z4 for each R, G, B is performed on the image data on the wafers W regarded as the inspection objects.

Then, when the Zernike coefficients Z1 to Z4 for each R, G, B are acquired from the image data on an n-th (n is a natural number) wafer W, whether or not each of the acquired Zernike coefficients Zi exceeds one of the upper limit threshold value and the lower limit threshold value of the feature amount is determined. When it is not determined that any of the Zernike coefficients Zi exceeds one of the upper limit threshold value and the lower limit threshold value, the Zernike coefficients Zi are acquired based on the image data on an n+1-th wafer W. Subsequently, determination whether or not each of the acquired Zernike coefficients Zi exceeds one of the upper limit threshold value and the lower limit threshold value is performed in sequence.

When it is determined that any of the Zernike coefficients Zi acquired from the image data on the n-th wafer W exceeds one of the upper limit threshold value and the lower limit threshold value, whether or not exceeding one of the upper limit threshold value and the lower limit threshold value has occurred successively over a predetermined number of times is determined about the Zernike coefficient Zi exceeding one of the upper limit threshold value and the lower limit threshold value (Step S1). When it is determined that the exceeding has not occurred successively over the predetermined number of times at Step S1, the Zernike coefficients Zi are acquired about the image data on the n+1-th wafer W, and determination whether or not each of the acquired Zernike coefficients Zi exceeds one of the upper limit threshold value and the lower limit threshold value is performed in sequence.

When it is determined that any of the Zernike coefficients Zi exceeds one of the upper limit threshold value and the lower limit threshold value successively over the predetermined number of times at Step S1, updating of the reference image data on the wafer W, the sensitivity parameter values, and the upper limit threshold values and the lower limit threshold values of the Zernike coefficients Zi is performed using the recently obtained image data on a predetermined number of wafers W of the image data on the wafers W accumulated in the data accumulating computer 3 (Step S2). In other words, Step S1 is repeatedly performed until it is determined that the Zernike coefficient Zi exceeds the upper limit threshold value or the lower limit threshold value successively over the predetermined number of times and Step S2 is performed.

Then, after the above execution of Step S2, actual inspection on the wafer W is restarted using the updated reference image data on the wafer W, sensitivity parameter values, and upper limit threshold values and lower limit threshold values of the Zernike coefficients Zi (Step S3). In other words, Step S1 is performed again using the updated reference image data on the wafer W, sensitivity parameter values, and upper limit threshold values and lower limit threshold values of the Zernike coefficients Zi. Steps S1 to S3 are executed by the above programs 42 to 46.

Figure 9:
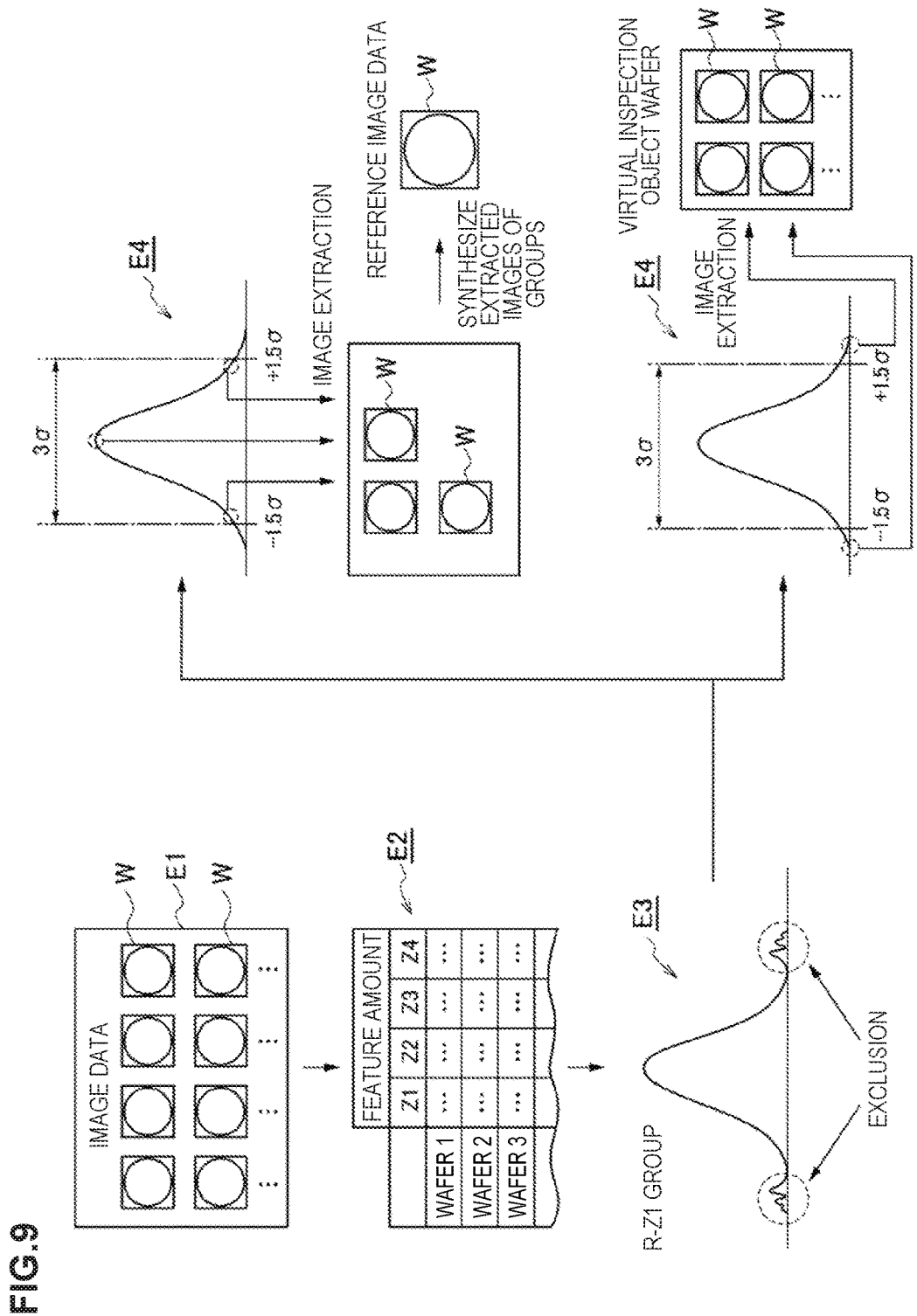
FIG. 9 is an explanatory view illustrating a procedure of obtaining reference image data on a wafer and image data on a wafer being a virtual inspection object.
Figure 10:
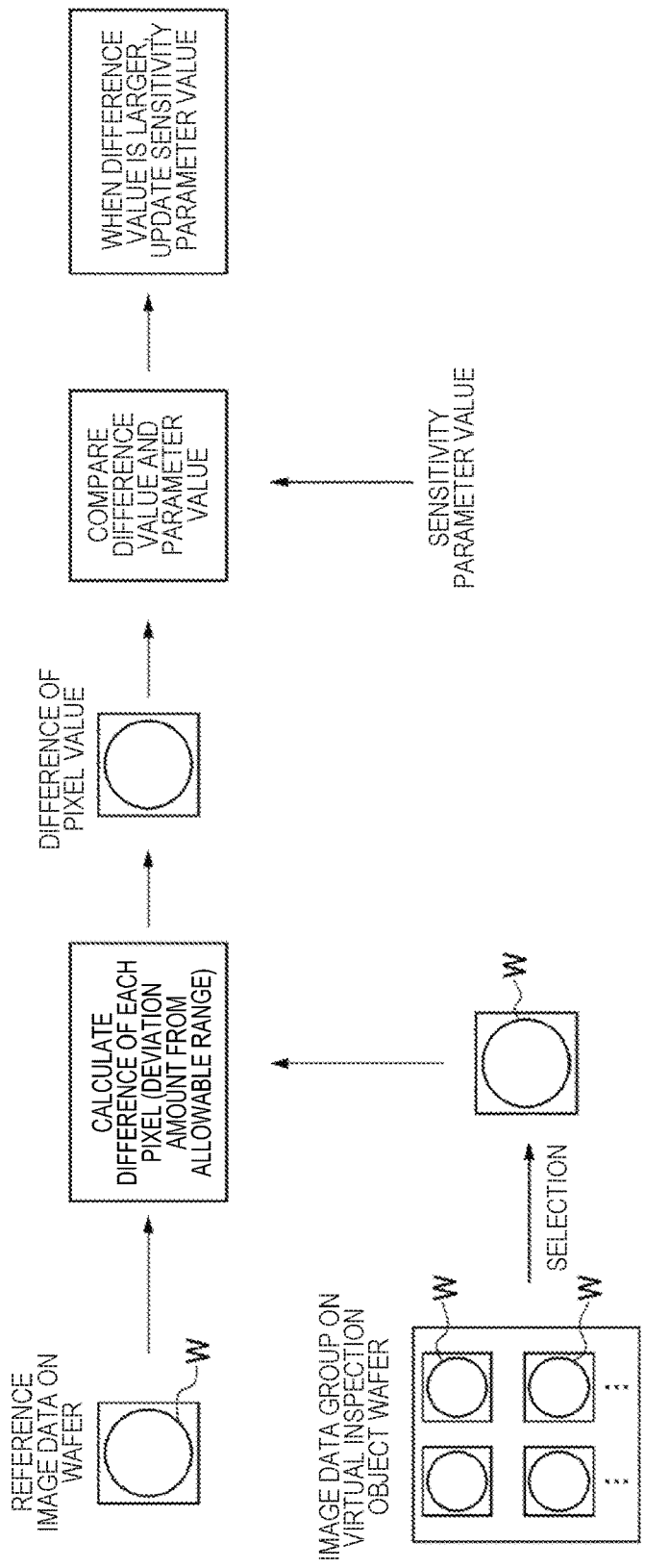
FIG. 10 is an explanatory view illustrating a procedure of virtual inspection.

Hereinafter, the concrete procedure of Step S2 in the above flow will be explained referring to the schematic diagrams in FIG. 9, FIG. 10. In this exemplary explanation, Step S2 is assumed to be performed using the image data on the wafers 1 to 100 illustrated in FIG. 7. An enclosure (indicated as E1) at an upper left portion in FIG. 9 illustrates the image data on the wafer 1 to the wafer 100 which have been obtained at Step S1 in the above flow, and Table E2 in front of an arrow from the enclosure E1 illustrates the feature amounts of the wafers acquired from the image data on the wafer 1 to the wafer 100. In short, Table E2 is the same as the table in FIG. 7 though illustration is simplified.

When Step S2 is started, the Zernike coefficients Zi being the acquired feature amounts which have the same degrees (numbers of terms) of the Zernike coefficients are extracted, and grouped for each R, G, B. FIG. 11 illustrates the feature amount of each group of R, G, B about Z1 as a representative. Hereinafter, similar processing is performed on each group. Hence, the processing to be performed on the group of the Zernike coefficient Z1 about R (called an R-Z1 group) as a representative will be explained. In FIG. 9, a normal distribution curve of the R-Z1 group is illustrated as E3 in front of an arrow from Table E2.

First of all, the deviation values on the normal distribution curve E3 are detected. The deviation values are the Zernike coefficients which are determined from the Zernike coefficients (the feature amounts) acquired from the image data on the wafer 1 to the wafer 100 in FIG. 7 and which are abnormally large or small when the Zernike coefficients of the R-Z1 group are expressed in a normal distribution, and as described later, the deviation values are the values regarded as a defective wafer W. Regions of the deviation values are illustrated by being surrounded by dashed line circles in the normal distribution curve E3. The wafer W corresponding to the deviation values is regarded as a defective wafer where a defect exists, and the Zernike coefficients of the defective wafer W are not used in the subsequent processing. A group made by excluding the Zernike coefficient Z1 of the defective wafer W from the R-Z1 group is illustrated as a defect-excluded R-Z1 group. In FIG. 9, a normal distribution curve created from the defect-excluded R-Z1 group is illustrated as E4.

Then, the image data on the wafer W having the Zernike coefficient Z1 closest to the average value is extracted regarding the Zernike coefficient Z1 in the defect-excluded R-Z1 group. Besides, the image data on the wafers W exhibiting the maximum value and the minimum value respectively among the Zernike coefficients Z1 included in a range of the average value of the Zernike coefficient Z1−1.5σ or more and the average value of the Zernike coefficient Z1+1.5σ or less are extracted. Note that σ is a standard deviation. Accordingly, schematically, the image data on the wafers W having the Zernike coefficient Z1 in the regions surrounded by the dashed line circles on the normal distribution curve E4 illustrated at an upper right in FIG. 9 are extracted.

Since similar processing is performed also on each group other than the R-Z1 group as explained above, extraction of the image data on the wafer W is performed also on each group similarly to the R-Z1 group. Many pieces of image data on the wafers W extracted from the groups are synthesized to create the reference image data on the wafer W. The synthesizing referred to here concretely means deciding the minimum value and the maximum value of the pixel value for each R, G, B from the image data on the selected wafers W for each pixel of the image data on the wafer W. The minimum value to the maximum value are set as the allowable range of the pixel value explained with FIG. 2, and the reference image data on the wafer W is created. When observing the values of the same Zernike coefficient about a plurality of wafers W, a wafer W group having a degree of separation smaller than the preset degree of separation from the average value of the Zernike coefficients of the plurality of wafers W is selected, and the reference image data on the wafer W is created based on the selected wafer W group. In other words, the reference image data is created using the image data on the wafer W having a least-likely possibility that it is a defective wafer W, among many pieces of image data.

Here, the defect-excluded R-Z1 group will be explained again. In this group, image data in the range of the average value of the Zernike coefficient Z1 in this group $-1.5\sigma$ or less and the average value of the Zernike coefficient $Z1+1.5\sigma$ or more are extracted as the image data on the wafers W being the virtual inspection objects. Specifically, image data having the Zernike coefficients Z1 respectively being the maximum value and the minimum value and the image data respectively having the Zernike coefficients Z1 being a value closest to the maximum value and a value closest to the minimum value are extracted as the image data on the wafers W being the virtual inspection objects. In this event, the extracted image data are schematically the image data on the wafers W corresponding to the regions surrounded by the dashed line circles on the normal distribution curve E4 illustrated at a lower right in FIG. 9.

The image data on the virtual inspection objects are extracted, similarly to the R-Z1 group, also from each group other than the R-Z1. More specifically, when observing the values of the same Zernike coefficient about a plurality of wafers W, the image data on a wafer W group having a degree of separation larger than the preset degree of separation, from the average value of the values of the Zernike coefficient of the plurality of wafers W is regarded as the image on the virtual inspection objects. Extracting the image data on the wafers W having the Zernike coefficients relatively largely separate from the average value as the image on the virtual inspection objects as explained above is to set, at the time when updating the sensitivity parameters D1 to D4 based on the result of virtual inspection as will be explained later, values enabling prevention, as much as possible, of a false defect in a range where detection of a defect can be securely performed in actual inspection.

Besides, at start of virtual inspection, the upper limit threshold values and the lower limit threshold values of the Zernike coefficients Zi corresponding to the group are reset from the group of Zernike coefficients. More specifically, the average value of the Zernike coefficient $Z1+1.5\sigma$ and the average value of the Zernike coefficient $Z1-1.5\sigma$ are acquired from the defect-excluded R-Z1 group, and these values are set as the upper limit threshold value and the lower limit threshold value of Z1 of R respectively.

When the reference image data and many pieces of image data on the virtual inspection object wafers W are obtained as explained above and the upper limit threshold values and the lower limit threshold values of the Zernike coefficients Zi are set, virtual inspection is executed. FIG. 10 illustrates the outline of the virtual inspection. First of all, the image data on one wafer W is selected from the image data on the virtual inspection object wafer W group, and comparison between the selected image data and the reference image data on the wafer W is performed as illustrated in the drawing. More specifically, as illustrated at the center of FIG. 10, the difference between the allowable range of the pixel value to be set as the reference image data about the pixel at each position and the pixel value of the inspection object wafer W (deviation amount from the allowable range) is calculated.

When the deviation amount is 0 in the pixels at all positions, the inspection object wafer W is determined to have no abnormality. Besides, when there is a pixel having a deviation amount that is not 0, the deviation amount of the pixel and the sensitivity parameter D set to be applied to the pixel (see FIG. 2) are compared as illustrated in FIG. 10. When the deviation amount is equal to or smaller than the sensitivity parameter D as a result of the comparison, the inspection object wafer W is determined to have no abnormality. When the deviation amount is larger than the sensitivity parameter D, whether or not the deviation amount exceeds the preset threshold value (as the final determination threshold value) is determined. The final determination threshold value has been preset, for example, for each of the sensitivity parameters D1 to D4 for each R, G, B. Then, when it is determined that the deviation amount does not exceed the final determination threshold value, the inspection object wafer W is determined to be a false defective wafer W which has a false defect if it is subjected to actual inspection. In other words, the wafer W is determined to be a wafer W actually having no defect. As explained above, the sensitivity parameter D used for the comparison is updated to have the above deviation amount so as to prevent the inspection object wafer W, when determined to be a false defective wafer W, from being determined to be a defective wafer W if the inspection object wafer W is subjected to actual inspection.

Then, when the virtual inspection object wafer W is determined to have no abnormality and when the virtual inspection object wafer W is determined to be a false defective wafer W, the upper limit threshold value and the lower limit threshold value of the Zernike coefficient Zi are updated to prevent the Zernike coefficient Zi acquired from the wafer W from exceeding the upper limit threshold value and the lower limit threshold value of the Zernike coefficient Zi when the virtual inspection object wafer W is subjected to actual inspection. The updating is performed such that both of the upper limit threshold value and the lower limit threshold value vary by the same numeric value, for example, to widen the allowable range of Zi between the upper limit threshold value and the lower limit threshold value. However, when the deviation amount exceeds the final determination threshold value in the comparison using the deviation amount and the final determination threshold value, the inspection object wafer W is determined to be a defective wafer W, and the updating of the sensitivity parameter D and the updating of the upper limit threshold value and the lower limit threshold value of the Zernike coefficient Zi are not performed.

Figure 12:
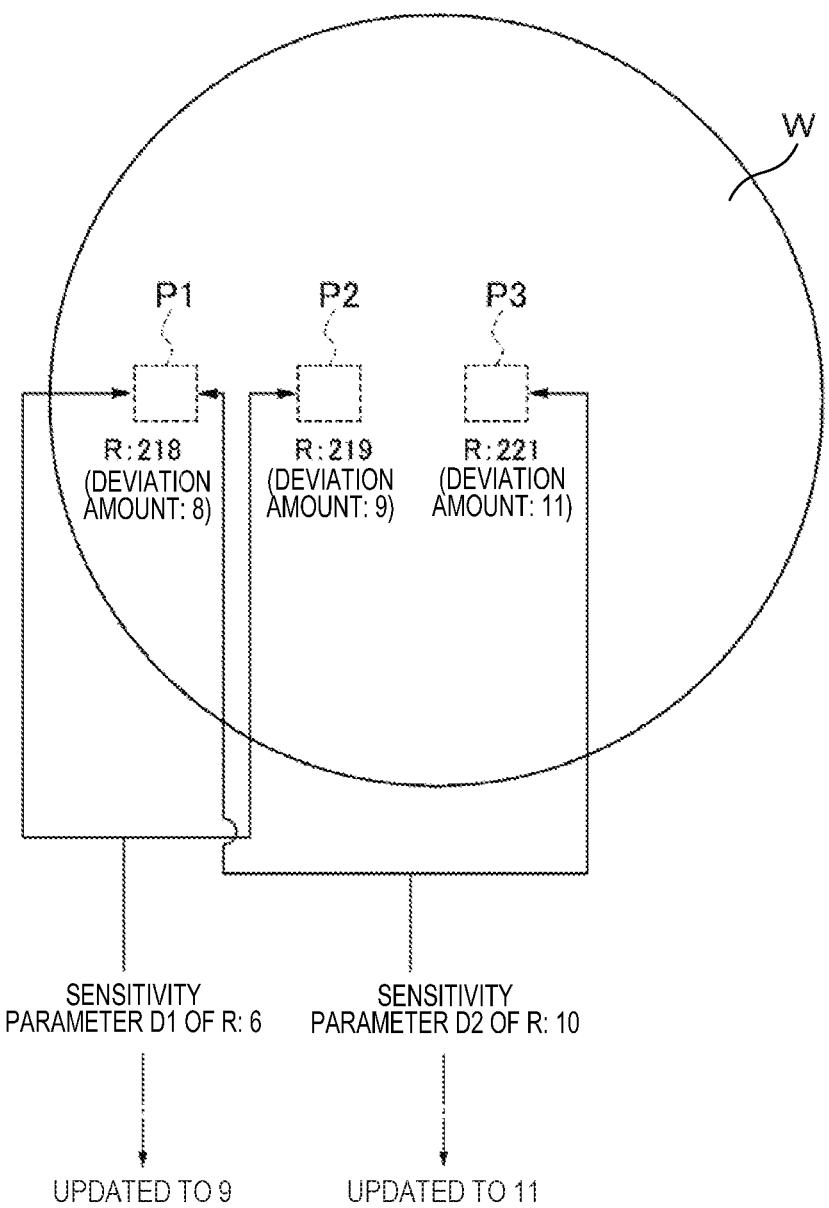
FIG. 12 is an explanatory view for illustrating the outline of virtual inspection.

An example of the updating of the sensitivity parameter D of R and the upper limit value and the lower limit value of the Zernike coefficient Z1 of R by the virtual inspection will be explained using concrete numeric values referring to FIG. 12. The image data on the inspection object wafer W in this explanation is the image data on the wafer W to be inspected as a first wafer W, and therefore it is assumed that the average value of the Zernike coefficient $Z1-1.5\sigma$ and the average value of the Zernike coefficient $Z1+1.5\sigma$ on the normal distribution curve E4 in FIG. 9 are set as the lower limit threshold value and the upper limit threshold value of the Zernike coefficient Z1 respectively. Here, for example, the lower limit threshold value is 160, and the upper limit threshold value is 170.

Besides, it is assumed that three pixels at positions different from one another in the image data are P1, P2, P3, and any of the allowable ranges for R at the pixels P1, P2, P3 in the reference image data on the wafer W is 200 to 210, and the final determination threshold value of each of the sensitivity parameters D1, D2 of R is 12. Further, it is also assumed that the Zernike coefficient Z1 of R about the inspection object wafer W is 158, and the Zernike coefficients Z1 of R at the pixels P1, P2, P3 in the image data on the virtual inspection object wafer W are 218, 219, 221 respectively. It is assumed that the sensitivity parameter D1 of R is 6 which is applied to the pixels P1, P2, but not applied to the pixel P3. Further, it is assumed that the sensitivity parameter D2 of R is 10, which is applied to the pixels P1, P3, but not applied to the pixel P2.

By performing virtual inspection, for example, under the above conditions, the deviation amounts from the allowable range of the reference image data on the wafer W are calculated for the pixel value in the image data on the virtual inspection object wafer W at the pixels P1, P2, P3. More specifically, 8 that is the difference between 200 to 210 and 218, 9 that is the difference between 200 to 210 and 219, and 11 that is the difference between 200 to 210 and 221 are calculated as the deviation amounts at the pixels P1, P2, P3 respectively. In other words, in this case, 8 that is the difference between 210 being the upper limit value of the allowable range and 218, 9 that is the difference between 210 being the upper limit value of the allowable range and 219, and 11 that is the difference between 210 being the upper limit value of the allowable range and 221 are calculated as the deviation amounts at the pixels P1, P2, P3 respectively.

In this case, 8, 9 being the deviation amounts at the pixels P1, P2 to which the sensitivity parameter D1 is applied are lower than 12 being the final determination threshold value. Further, 8, 11 being the deviation amounts at the pixels P1, P3 to which the sensitivity parameter D2 is applied are lower than 12 being the final determination threshold value.

Accordingly, the inspection object wafer W is determined to be a false defective wafer W. Besides, the sensitivity parameter D1 is updated to 9 that is larger of 8, 9 being the deviation amounts and the sensitivity parameter D2 is updated, for example, to 11 being the deviation amount to prevent the inspection object wafer W from being determined to be a defective wafer W in actual inspection. Though correction (updating) of only the sensitivity parameters D1, D2 are illustrated to prevent complication of explanation, the sensitivity parameters D3, D4 are also updated, similarly to the sensitivity parameters D1, D2, to be able to prevent the false defect according to the result of virtual inspection. Further, inspection is performed, similarly to P1 to P3, also on the pixels at other positions.

Then, the inspection object wafer W is determined to be a false defective wafer W, namely, to be not a defective wafer W, and therefore the upper limit threshold value and the lower limit threshold value of the Zernike coefficient Z1 of R are also updated. Since the allowable range of the Zernike coefficient Z1 between the upper limit threshold value and the lower limit threshold value is 170 to 160 and the Zernike coefficient Z1 of the inspection object wafer W is 158 which is separated from the allowable range by 2, the upper limit threshold value and the lower limit threshold value each vary by 2, so that the upper limit threshold value is updated to 172 and the lower limit threshold value is updated to 158. The upper limit threshold value and the lower limit threshold value set for the Zernike coefficient other than the Zernike coefficient Z1 of R are updated similarly to the upper limit threshold value and the lower limit threshold value for the Zernike coefficient Z1 of R. Note that though inspection is illustrated to be performed while taking only the pixel value of R of R, G, B of the image data on the inspection object wafer W to prevent complication of illustration and explanation, in the virtual inspection schematically illustrated in FIG. 12, inspection is similarly performed also on G, B other than R as in actual inspection. Then, based on the inspection result of the virtual inspection, updating of the sensitivity parameters D and the threshold values (the upper limit threshold values and the lower limit threshold values) of the Zernike coefficients Zi is performed.

The above virtual inspection is performed in sequence on the image data on all of the wafers W extracted as the virtual inspection objects, and the sensitivity parameters D1 to D4 and the threshold values of the Zernike coefficients Zi are sequentially updated. Accordingly, when the sensitivity parameters D1 to D4 have been updated as the result of the prior virtual inspection, the updated sensitivity parameters D1 to D4 are used in next virtual inspection. Note that the sensitivity parameters D1 to D4 and the threshold values of the Zernike coefficients Zi calculated in execution of Step S2 are candidate values of the sensitivity parameters D1 to D4 and the threshold values of the Zernike coefficients Zi at that stage. Then, the candidate values of the sensitivity parameters D1 to D4 and the threshold values of the Zernike coefficients Zi which are finally acquired after completion of virtual inspection on all the image data are decided as the sensitivity parameters D1 to D4 and the threshold values of the Zernike coefficients Zi to be used in actual inspection at Step S3 in the above flow.

Figure 13:
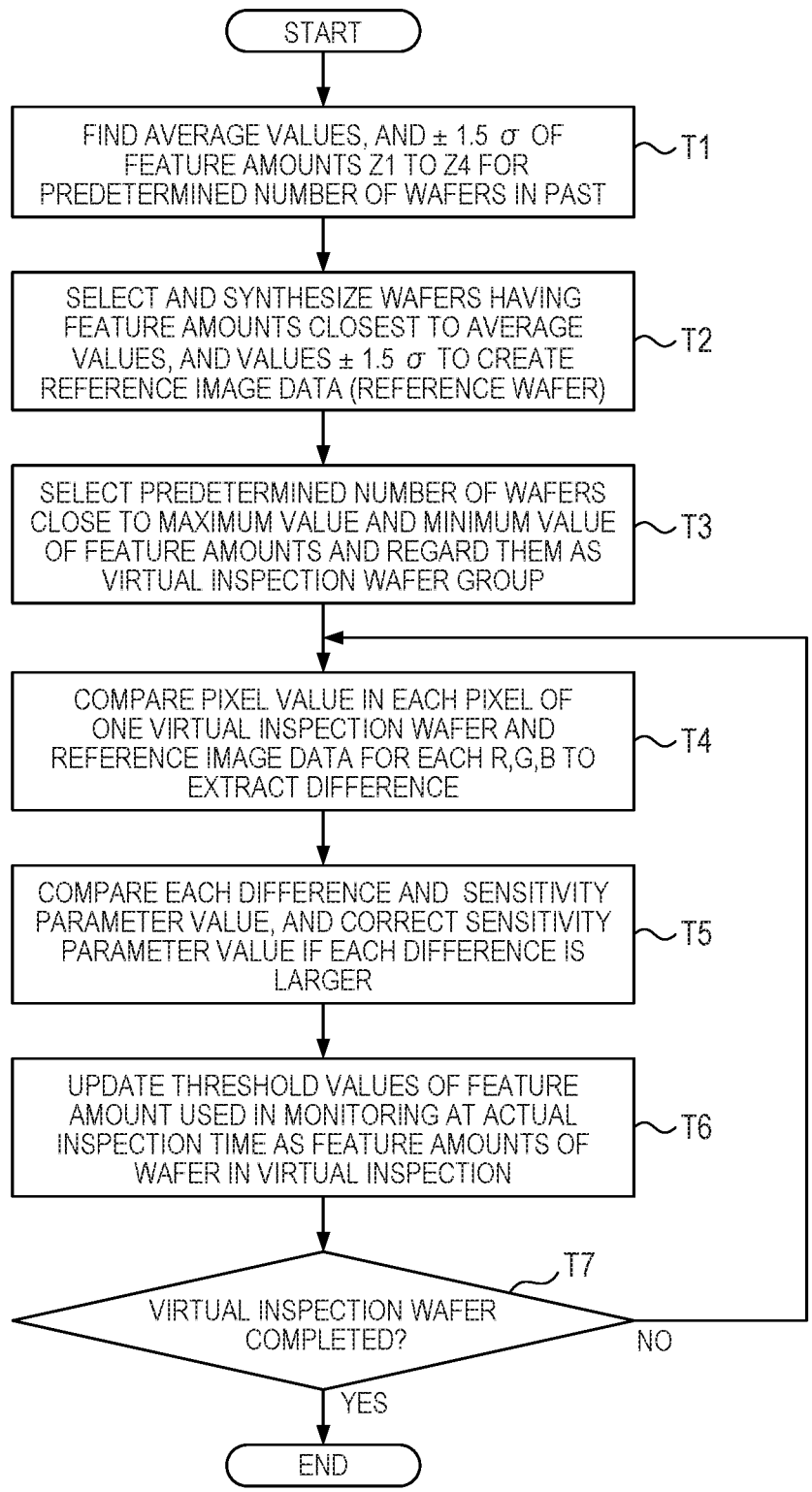
FIG. 13 is a flowchart of virtual inspection performed to set parameters for performing defect inspection.

Hereinafter, explanation will be made referring to FIG. 13 being a flow in which the above processing at Step S2 is put together. First of all, the image data on the wafer W regarded as being defective is excluded from the image data on a predetermined number of wafers W obtained in the past and stored in the data accumulating computer 3, and then the average values of the Zernike coefficients Z1 to Z4 being feature amounts of the wafer W and the average value±1.5σ are calculated (Step T1). Then, wafers having Zernike coefficients closest to the average values and the average value±1.5σ are selected and synthesized to create the reference image data on the wafer W (image data on a reference wafer) (Step T2). Subsequently, a predetermined number of wafers having Zernike coefficients close to each of the maximum value and the minimum value are selected and regarded as an inspection object wafer group (Step T3). In short, Steps T1 to T3 are steps of performing the processing explained with FIG. 9.

Then, the pixel value at each pixel of one selected virtual inspection object wafer and the pixel value in the allowable range in the reference image data are compared for each R, G, B to calculate the difference (deviation amount from the allowable range) (Step T4). Each difference and the sensitivity parameter value are compared, and the sensitivity parameter value is corrected if each difference is larger (Step T5), and the upper limit threshold value and the lower limit threshold value of the Zernike coefficient are updated based on the Zernike coefficient of the virtual inspection object wafer (Step T6). In short, Steps T4 to T6 are steps of performing the processing explained with FIG. 10, FIG. 12. Thereafter, whether or not virtual inspection has been completed on all of the wafers W extracted as the virtual inspection object wafers is determined (Step T7), and when it is determined that virtual inspection has been completed, Step S3 in the above flow explained with FIG. 8 is executed. In other words, actual inspection is started. When it is determined that virtual inspection has not been completed on all of the wafers W, steps of Step T4 and subsequent thereto are performed on uninspected wafers W.

According to the coating and developing apparatus 1, the image data obtained by picking up an image of the entire front surface of the wafer W and the reference pixel data on the wafer W are compared and the sensitivity parameters D1 to D4 for determining whether or not the wafer W is defective are automatically adjusted.

More specifically, a plurality of virtual inspection wafers W are selected from among a plurality of wafers W inspected earlier than the adjustment time of the sensitivity parameters D1 to D4, and subjected to virtual inspection by comparing with new reference image data on the wafer W after the adjustment of the sensitivity parameters D1 to D4. When a certain wafer W is determined to be a false defective wafer W, the sensitivity parameters D1 to D4 are eased so as to prevent the wafer W from being determined to be a defective wafer W in actual inspection.

Then, this operation is performed in sequence on the plurality of selected virtual inspection wafers W, and finally acquired sensitivity parameters D1 to D4 are used as new sensitivity parameters D1 to D4. Accordingly, it is possible to reduce the labor and time required for adjustment of the sensitivity parameters D1 to D4, and to realize stable defect inspection on the wafer W while suppressing occurrence of a false defect.

The updating of the sensitivity parameter is not limited to be performed by monitoring whether or not the feature amount Z exceeds the threshold value as explained above. The updating of the sensitivity parameter may be started, for example, when actual inspection on wafers W in a predetermined number of lots from the recent updating time is completed, may be started when actual inspection on a predetermined number of wafers W from the recent updating time is completed, may be started when a predetermined number of days elapses from the recent updating time, or may be started by an instruction of an operator. Besides, the number of defects within the plane of the wafer W is stored in actual inspection, the number of defects is accumulated every time actual inspection is performed, and when the number of accumulated defects exceeds a predetermined threshold value, the updating may be started.

Further, the image data on one wafer W obtained first is regarded as the reference image data, actual inspection is performed on a plurality of wafers W using the reference image data, and then creation of new reference image data on the wafer W and updating of the sensitivity parameters D may be performed at a certain point in time using the image data obtained from the above plurality of wafers W.

In the above example, the image data on the wafer W having a degree of separation smaller than the preset degree of separation from the average value of the feature amount Z is regarded as image data for creating the reference image data, the image data on the wafer W having a degree of separation larger than the preset degree of separation from the average value of the feature amount Z is regarded as image data for virtual inspection object, and each degree of separation is set based on the standard deviation of the feature amount Z, but the degree of separation may be set based on the average deviation of the feature amount Z.

Preferred embodiments of the present invention have been described above with reference to the accompanying drawings, but the present invention is not limited to the embodiments. It should be understood that various changes and modifications are readily apparent to those skilled in the art within the scope of the spirit as set forth in claims, and those should also be within the technical scope of the present invention.

What is claimed is:

1. A substrate defect inspection apparatus for inspecting a substrate for a defect, configured to compare, for each pixel value of image data obtained by picking up an image of an entire front surface of a substrate being an inspection object, using reference pixel data made by associating each position and an allowable range of the pixel value, a deviation amount from the allowable range and a sensitivity parameter value being an allowable deviation amount when each pixel value is deviated from the allowable range corresponding to the position thereof, and determine the substrate to be a defective substrate when the deviation amount exceeds the sensitivity parameter value, the substrate defect inspection apparatus comprising:
    a computer configured to:
        create, at adjustment time of the sensitivity parameter value, reference pixel data to be used after the adjustment;
        adjust, in an adjustment unit for the sensitivity parameter value, the sensitivity parameter value; and
        select, in a virtual inspection substrate selection unit, a plurality of virtual inspection substrates which are used for adjusting the sensitivity parameter value and on which a virtual inspection being inspection for adjusting the sensitivity parameter value is to be performed by comparison with the reference pixel data, from among a plurality of substrates inspected earlier than the adjustment time of the sensitivity parameter value,
    wherein the adjustment unit for the sensitivity parameter value is configured to execute, in the virtual inspection, for each of the selected virtual inspection substrates:
        a first step of comparing, for each pixel value of the selected virtual inspection substrate, using the reference pixel data to be used after the adjustment, the deviation amount from the allowable range and the sensitivity parameter value before the adjustment when each pixel value is deviated from the allowable range corresponding to the position thereof; and
        a second step of updating the deviation amount as a new sensitivity parameter value when the deviation amount exceeds the sensitivity parameter value and the deviation amount is equal to or less than a threshold value;
    wherein the first step and the second step are performed in sequence on image data on the plurality of substrates inspected earlier, and
    when the sensitivity parameter value being an object to be compared with the deviation amount has been updated, storing in a storage unit a finally updated sensitivity parameter value as the sensitivity parameter value after the adjustment for use in a next actual inspection.

2. The substrate defect inspection apparatus according to claim 1,
    wherein each pixel value of the image data obtained by picking up the image of the entire front surface of the substrate being an inspection object is a pixel value of each of R (red), G (green), B (blue) being three primary colors, and
    wherein the reference pixel data is data made by associating each position and the allowable range of the pixel value for each R, G, B.

3. The substrate defect inspection apparatus according to claim 1,
    wherein the computer is configured to acquire a Zernike coefficient by decomposing a planar distribution of pixels by a Zernike function on each of the plurality of substrates inspected earlier than the adjustment time of the sensitivity parameter value, select a substrate group having a degree of separation smaller than a preset degree of separation from an average value of the plurality of substrates regarding the same Zernike coefficient of each substrate, and create reference pixel data, based on the selected substrate group.

4. The substrate defect inspection apparatus according to claim 1,
wherein the computer is configured to acquire a Zernike coefficient by decomposing a planar distribution of pixels by a Zernike function on each of the plurality of substrates inspected earlier than the adjustment time of the sensitivity parameter value, and select a substrate group having a degree of separation larger than a preset degree of separation from an average value of Zernike coefficients of the plurality of substrates regarding the same Zernike coefficient of each substrate.

5. The substrate defect inspection apparatus according to claim 4, wherein the computer is further configured to
acquire, by a monitoring unit, a feature point being the Zernike coefficient by decomposing the planar distribution of the pixels by a Zernike function for a substrate being an inspection object to be actually inspected after the adjustment of the sensitivity parameter value, monitor whether or not the feature point is deviated from a predetermined threshold value, and decide timing for adjusting the sensitivity parameter value, based on a result of the monitoring; and
create, by a monitoring threshold value creation unit, the monitoring threshold value used in the monitoring unit, and
wherein the monitoring threshold value creation unit performs, on the selected virtual inspection substrate, at virtual inspection time performed at the adjustment time of the sensitivity parameter value:
first determination of determining whether or not the pixel value is deviated from the allowable range;
second determination of determining whether or not the deviation amount from the allowable range exceeds the sensitivity parameter value even if the pixel value is deviated from the allowable range; and
decision of regarding the feature point of the substrate as a candidate of the monitoring threshold value when the difference between the deviation amount and the sensitivity parameter value is equal to or less than the threshold value even if the deviation amount exceeds the sensitivity parameter value, and
perform the first determination, the second determination, and the decision in sequence on a group of the selected virtual inspection substrates, and decide a finally acquired candidate value as the monitoring threshold value.

6. The substrate defect inspection apparatus according to claim 1,
wherein the sensitivity parameter value is decided according to a region of the substrate.

7. A method of adjusting a sensitivity parameter value for substrate defect inspection used in a substrate defect inspection apparatus, configured to compare, for each pixel value of image data obtained by picking up an image of an entire front surface of a substrate being an inspection object, using reference pixel data made by associating each position and an allowable range of the pixel value, a deviation amount from the allowable range and a sensitivity parameter value being an allowable deviation amount when each pixel value is deviated from the allowable range corresponding to the position thereof, and determine the substrate to be a defective substrate when the deviation amount exceeds the sensitivity parameter value, the method comprising:
a step of creating, at adjustment time of the sensitivity parameter value, reference pixel data to be used after the adjustment;
a step of adjusting the sensitivity parameter value;
a step of selecting a virtual inspection substrate which is used for adjusting the sensitivity parameter value and on which a virtual inspection is to be performed by comparison with the reference pixel data, from among a plurality of substrates inspected earlier than the adjustment time of the sensitivity parameter value,
wherein the step of adjusting performs, for the selected virtual inspection substrate:
a step of comparing, for each pixel value of the selected virtual inspection substrate, using the reference pixel data to be used after the adjustment, the deviation amount from the allowable range and the sensitivity parameter value before the adjustment when each pixel value is deviated from the allowable range corresponding to the position thereof; and
a step of updating the deviation amount as a new sensitivity parameter value when the deviation amount exceeds the sensitivity parameter value and the deviation amount is equal to or less than a threshold value;
wherein the steps of comparing and updating are performed in sequence on image data on the plurality of substrates inspected earlier, and
when the sensitivity parameter value being an object to be compared with the deviation amount has been updated, storing in a storage unit a finally updated sensitivity parameter value as the sensitivity parameter value after the adjustment for use in a next actual inspection.

8. The method of adjusting a sensitivity parameter value for substrate defect inspection according to claim 7,
wherein each pixel value of the image data obtained by picking up the image of the entire front surface of the substrate being an inspection object is a pixel value of each of R (red), G (green), B (blue) being three primary colors, and
wherein the reference pixel data is data made by associating each position and the allowable range of the pixel value for each R, G, B.

9. A non-transitory storage medium storing a computer program to execute a method of adjusting a sensitivity parameter value for substrate defect inspection in a substrate defect inspection apparatus,
the method of adjusting a sensitivity parameter value for substrate defect inspection, configured to compare, for each pixel value of image data obtained by picking up an image of an entire front surface of a substrate being an inspection object, using reference pixel data made by associating each position and an allowable range of the pixel value, a deviation amount from the allowable range and a sensitivity parameter value being an allowable deviation amount when each pixel value is deviated from the allowable range corresponding to the position thereof, and determine the substrate to be a defective substrate when the deviation amount exceeds the sensitivity parameter value, comprising:
a step of creating, at adjustment time of the sensitivity parameter value, reference pixel data to be used after the adjustment;
a step of adjusting the sensitivity parameter value;

a step of selecting a virtual inspection substrate which is used for adjusting the sensitivity parameter value and on which a virtual inspection is to be performed by comparison with the reference pixel data, from among a plurality of substrates inspected earlier than the adjustment time of the sensitivity parameter value, wherein the step of adjusting performs, for the selected virtual inspection substrate:

a step of comparing, for each pixel value of the selected virtual inspection substrate, using the reference pixel data to be used after the adjustment, the deviation amount from the allowable range and the sensitivity parameter value before the adjustment when each pixel value is deviated from the allowable range corresponding to the position thereof; and a step of updating the deviation amount as a new sensitivity parameter value when the deviation amount exceeds the sensitivity parameter value and the deviation amount is equal to or less than a threshold value;

wherein the steps of comparing and updating are performed in sequence on image data on the plurality of substrates inspected earlier, and when the sensitivity parameter value being an object to be compared with the deviation amount has been updated, storing in a storage unit a finally updated sensitivity parameter value as the sensitivity parameter value after the adjustment for use in a next actual inspection.

\* \* \* \* \*